(12) United States Patent
Xu et al.

(10) Patent No.: US 11,266,388 B2
(45) Date of Patent: Mar. 8, 2022

(54) FLEXIBLE SURGICAL INSTRUMENT WITH STRUCTURAL BONES IN A CROSSED ARRANGEMENT

(71) Applicant: BEIJING SURGERII TECHNOLOGY CO., LTD., Beijing (CN)

(72) Inventors: Kai Xu, Beijing (CN); Zhengchen Dai, Beijing (CN); TianLai Dong, Beijing (CN); Jiangran Zhao, Beijing (CN); Huan Liu, Beijing (CN); Bo Liang, Beijing (CN); Zhixiong Yang, Beijing (CN); Zhijun Zhu, Beijing (CN)

(73) Assignee: BEIJING SURGERII TECHNOLOGY CO., LTD., Beijing (CN)

( * ) Notice: Subject to any disclaimer, the term of this patent is extended or adjusted under 35 U.S.C. 154(b) by 218 days.

(21) Appl. No.: 16/329,740

(22) PCT Filed: Aug. 31, 2017

(86) PCT No.: PCT/CN2017/099851
§ 371 (c)(1),
(2) Date: Feb. 28, 2019

(87) PCT Pub. No.: WO2018/041201
PCT Pub. Date: Mar. 8, 2018

(65) Prior Publication Data
US 2019/0192128 A1    Jun. 27, 2019

(30) Foreign Application Priority Data

Aug. 31, 2016 (CN) .......................... 201610799314.1
Aug. 31, 2016 (CN) .......................... 201610799332.X

(51) Int. Cl.
*A61B 17/00* (2006.01)
*A61B 34/30* (2016.01)
(Continued)

(52) U.S. Cl.
CPC ........ *A61B 17/00234* (2013.01); *A61B 17/00* (2013.01); *A61B 17/29* (2013.01);
(Continued)

(58) Field of Classification Search
CPC .... A61B 2017/003; A61B 2017/00305; A61B 2017/00314; A61B 2017/00318;
(Continued)

(56) References Cited

U.S. PATENT DOCUMENTS

2002/0087048 A1    7/2002    Brock et al.
2011/0163146 A1    7/2011    Ortiz et al.
(Continued)

FOREIGN PATENT DOCUMENTS

CN    103085083 A    5/2013
CN    103315781 A    9/2013
(Continued)

OTHER PUBLICATIONS

State Intellectual Property Office of the People's Republic of China, First Search Issued in Application No. 201610799332.X, dated Mar. 16, 2018, 4 pages.
(Continued)

*Primary Examiner* — Elizabeth Houston
*Assistant Examiner* — Lindsey Bachman
(74) *Attorney, Agent, or Firm* — McCoy Russell LLP

(57) ABSTRACT

A flexible surgical instrument has structural backbones in crossed arrangement, the flexible surgical instrument includes a flexible continuum structure comprising a distal structure, a proximal structure and a middle connection body; the distal structure includes a first distal segment and
(Continued)

a second distal segment, the proximal structure includes a proximal segment; first segment structural backbone(s) on the proximal segment and first segment structural backbone(s) on the first distal segment are fixedly connected respectively one to one or are of the same structural backbone; second segment structural backbone(s) on the proximal segment and second segment structural backbone(s) the second distal segment are fixedly connected respectively one to one or are of the same structural backbone; the middle connection body includes two passage fixing plates, between which structural backbone guiding passage(s) and structural backbone cross guiding passage(s) are fixedly connected; the first segment structural backbone(s) (163, 123) extends through the structural backbone cross guiding passage(s) (153), the second segment structural backbone(s) extends through the structural backbone guiding passage(s).

15 Claims, 11 Drawing Sheets

(51) Int. Cl.
*A61B 17/29* (2006.01)
*B25J 1/02* (2006.01)
*B25J 19/02* (2006.01)

(52) U.S. Cl.
CPC .............. *A61B 34/30* (2016.02); *B25J 1/02* (2013.01); *A61B 2017/00305* (2013.01); *A61B 2017/2905* (2013.01); *A61B 2017/2912* (2013.01); *A61B 2034/301* (2016.02); *B25J 19/02* (2013.01)

(58) Field of Classification Search
CPC ........... A61B 2017/00323; A61B 2017/00327; A61B 2017/0034; A61B 2017/2905; A61B 34/30–37; A61B 34/71; A61B 2034/301–306; A61B 17/00234; A61B 2017/00238–00362; A61B 17/29–295; A61B 17/00; A61B 2017/00367; A61B 2017/2912; A61B 2017/2927; A61B 2017/2929; A61B 1/0055; A61B 2034/715; B25J 9/104; B25J 9/106; B25J 1/02; B25J 9/02; B25J 18/06
See application file for complete search history.

(56) References Cited

U.S. PATENT DOCUMENTS

| | | | |
|---|---|---|---|
| 2013/0090763 A1* | 4/2013 | Simaan | A61B 5/11 |
| | | | 700/258 |
| 2015/0216546 A1 | 8/2015 | Krause et al. | |
| 2015/0352728 A1* | 12/2015 | Wang | A61B 1/00 |
| | | | 74/490.04 |

FOREIGN PATENT DOCUMENTS

| | | |
|---|---|---|
| CN | 103707322 A | 4/2014 |
| CN | 103732161 A | 4/2014 |
| CN | 104883991 A | 9/2015 |
| CN | 104887313 A | 9/2015 |
| CN | 106175852 A | 12/2016 |
| CN | 106361387 A | 2/2017 |
| EP | 2008594 A2 | 12/2008 |
| JP | 2009136684 A | 6/2009 |
| JP | 2012525916 A | 10/2012 |
| WO | 9910137 A1 | 3/1999 |
| WO | 2006057702 A2 | 6/2006 |
| WO | 2009001054 A1 | 12/2008 |
| WO | 2011108840 A2 | 9/2011 |
| WO | 2015126752 A1 | 8/2015 |
| WO | 2015153111 A1 | 10/2015 |

OTHER PUBLICATIONS

State Intellectual Property Office of the People's Republic of China, Office Action and Search Report Issued in Application No. 201610799314.1, dated May 3, 2018, 9 pages.
European Patent Office, Supplementary European Search Report Issued in Application No. 17845503.6, dated Apr. 6, 2020, Germany, 2 pages.
China National Intellectual Property Administration, Supplementary Search Issued in Application No. 201610799314.1, dated Dec. 7, 2018, 3 pages.
ISA State Intellectual Property Office of the People's Republic of China, International Search Report Issued in Application No. PCT/CN2017/099851, dated Dec. 7, 2017, WIPO, 4 pages.

* cited by examiner

FLEXIBLE SURGICAL INSTRUMENT WITH STRUCTURAL BONES IN A CROSSED ARRANGEMENT

CROSS REFERENCE TO RELATED APPLICATIONS

The present patent application is a U.S. national phase of Chinese International Application No. PCT/CN2017/099851 entitled "FLEXIBLE SURGICAL INSTRUMENT WITH STRUCTURAL BONES IN A CROSSED ARRANGEMENT" and filed on Aug. 31, 2017. Chinese International Application No. PCT/CN2017/099851 claims priority to benefits of a Chinese Patent Application No. 201610799332.X, filed on Aug. 31, 2016 and Chinese Patent Application No. 201610799314.1, filed on Aug. 31, 2016. The entire contents of each of the above-identified application are hereby incorporated by reference for all purposes.

FIELD OF THE DISCLOSURE

The present invention relates to a flexible surgical instrument with structural backbones in a crossed arrangement, which belongs to the field of medical instrument.

BACKGROUND

In modern medical field, manual laparoscopic minimally invasive surgery (MIS) with several ports is clinically applied broadly. Such kind of MIS successfully reduces postoperative pains, complications, period for stay and recovery, as well as postoperative scars in appearance, for the patients. In order to further reduce surgical invasiveness, reduce the patient's pain, researchers have proposed a laparoscope MIS with a single port.

In contrast to the laparoscopic MIS with multi ports, which need to create several surface incisions, during the laparoscopic MIS with single port, all the surgical instruments enter into the abdominal cavity though one surface incision (typically umbilicus), thus further reduce trauma made to the patient. However, such a configuration of single port proposes more restricted requirements in terms of both design for the surgical instrument and the operation of the surgeon during surgery.

Traditional rigid surgical instruments are mostly elongated rod-like structure, with a surgical end effector provided at the tip of the instrument, and its movement is controlled by pulling wires or cables. For the manual laparoscope MIS with the single-port setup based on traditional rigid surgical instrument, because of the requirement on complex coordination between hands and eyes during operation, and in view of the difficulties that the surgical instrument has limited flexibility, and a narrow working range, the manual single-port laparoscopic MIS is yet not broadly clinically applied.

SUMMARY

In view of the above technical problem, one object of the present invention is providing a flexible surgical instrument with structural backbones in a crossed arrangement, the flexible surgical instrument can be well applied in surgeries carried out through a single surgical incision or a plurality of surgical incisions.

In order to achieve the above mentioned object, the present application proposes the following solution: A flexible surgical instrument with structural backbones in a crossed arrangement, the flexible surgical instrument includes a flexible continuous body structure comprising a distal structural body, a proximal structural body and a middle connecting body;

the distal structural body includes a first distal segment and a second distal segment; the first distal segment includes a first distal spacing disk, a first distal fixing disk and first distal segment structural backbones; the second distal segment includes a second distal spacing disk, a second distal fixing disk and a second distal segment structural backbones; the proximal structural body includes a proximal segment including a proximal spacing disk, a proximal fixing disk, first proximal segment structural backbones and second proximal segment structural backbones;

one end of each the first proximal segment structural backbones on the proximal segment and one end of each the first distal segment structural backbones on the first distal segment are fixedly connected to each other, or each the first proximal segment structural backbones on the proximal segment and corresponding first distal segment structural backbone on the first distal segment is the same structural backbone; one end of each the second proximal segment structural backbones on the proximal segment and one end of each the second distal segment structural backbones on the second distal segment are fixedly connected to each other, or each the second proximal segment structural backbones on the proximal segment and corresponding second distal segment structural backbone on the second distal segment is the same structural backbone;

the middle connecting body includes two passage fixing plates, structural backbone guiding passages and structural backbone cross guiding passages are fixedly connected between the two passage fixing plates, respectively; one end of each the first proximal segment structural backbones are fixedly connected to the proximal fixing disk, and the other end thereof are fixedly connected to the first distal fixing disk after passing through the proximal spacing disk, the structural backbone cross guiding passages and the first distal spacing disk in sequence;

one end of each the second proximal segment structural backbones are fixedly connected to the proximal fixing disk, and the other end thereof are fixedly connected to the second distal fixing disk after passing through the proximal spacing disk, the structural backbone guiding passages, the first distal segment and the second distal spacing disk;

the structural backbone cross guiding passages are in a left-right crossed arrangement in a horizontal direction, or in an upper-lower crossed arrangement in a vertical direction, so that the first proximal segment structural backbone at the left part of the proximal segment connects with the first distal segment structural backbone at the right part of the first distal segment, and the first proximal segment structural backbone at the right part of the proximal segment connects with the first distal segment structural backbone at the left part of the first distal segment, or the first proximal segment structural backbone at the upper part of the proximal segment connects with the first distal segment structural backbone at the lower part of the first distal segment, and the first proximal segment structural backbone at the lower part of the proximal segment connects with the first distal segment structural backbone at the upper part of the first distal segment.

In a preferred embodiment, the flexible surgical instrument may further include a driving handle including a driving handle base, a gimbal and a linear sliding module; the driving handle base passes through the proximal structural body and connects to one of the two passage fixing plates via the gimbal; the driving handle base connects to the proximal fixing disk via the linear sliding module.

In a preferred embodiment, the linear sliding module includes a track and a slider slidably connected on the track, the track is fixedly connected on the driving handle base, the slider is fixedly connected to the proximal fixing disk.

In a preferred embodiment, a surgical end effector is provided at a distal end of the distal structural body, at least one control wire for the surgical end effector extends through the distal structural body, the other end connects to a surgical end effector driving mechanism provided on the driving handle base.

In a preferred embodiment, the surgical end effector driving mechanism includes a horizontal guide rod, a horizontal moving slider, a link, a vertical guide rod and a vertical moving slider, wherein the vertical guide rod is fixedly connected to the driving handle base and is perpendicular to the axial direction of the driving handle base, the vertical moving slider is slidably connected to the vertical guide rod, the horizontal guide rod is fixedly connected to the driving handle base and is parallel to the axial direction of the driving handle base, the horizontal moving slider is slidably connected to the horizontal guide rod, the horizontal moving slider is located distal to the vertical guide rod, the vertical moving slider connects to the horizontal moving slider via the link; a spring is sleeved on the vertical guide rod, one end of the spring is fixedly connected to the driving handle base, and the other end thereof is fixedly connected to the vertical moving slider; the horizontal moving slider is fixedly connected to one end of the at least one control wire.

In a preferred embodiment, at least one control wire guiding passage is provided between the passage fixing plates, the at least one control wire extends through the at least one control wire guiding passage.

In a preferred embodiment, the flexible surgical instrument may further comprises a driving handle cover and a flexible surgical instrument housing; the driving handle cover is fixedly connected to the driving handle base; the middle connection body and the proximal structural body both locate within the flexible surgical instrument housing, the two passage fixing plates are fixedly connected to the flexible surgical instrument housing; a chute for rotation of the driving handle is provided at a proximal end of the flexible surgical instrument housing.

In a preferred embodiment, the chute is in a cross shape.

The present invention further provides a flexible surgical instrument with structural backbones in a crossed arrangement, the flexible surgical instrument includes a flexible continuous body structure comprising a distal structural body, a proximal structural body and a middle connecting body;

the distal structural body includes a first distal segment and a second distal segment; the first distal segment includes a first distal spacing disk, a first distal fixing disk and first distal segment structural backbones; the second distal segment includes a second distal spacing disk, a second distal fixing disk and second distal segment structural backbones; the proximal structural body includes a proximal segment including a proximal spacing disk, a proximal fixing disk, first proximal segment structural backbones and second proximal segment structural backbones;

one end of each the first proximal segment structural backbones on the proximal segment and one end of each the first distal segment structural backbones on the first distal segment are fixedly connected to each other, or each the first proximal segment structural backbones on the proximal segment and corresponding first distal segment structural backbone on the first distal segment is the same structural backbone; one end of each the second proximal segment structural backbones on the proximal segment and the second distal segment structural backbones on the second distal segment are fixedly connected to each other, or each the second proximal segment structural backbones on the proximal segment and corresponding second distal segment structural backbone on the second distal segment is the same structural backbone;

the middle connecting body includes two passage fixing plates, structural backbone guiding passages and structural backbone cross guiding passages are fixedly connected between the two passage fixing plates, respectively;

one end of each the first proximal segment structural backbones are fixedly connected to the proximal fixing disk, and the other end thereof are fixedly connected to the first distal fixing disk after passing through the proximal spacing disk, the structural backbone cross guiding passages and the first distal spacing disk in sequence; one end of each the second proximal segment structural backbones are fixedly connected to the proximal fixing disk, and the other end thereof are fixedly connected to the second distal fixing disk after passing through the proximal spacing disk, the structural backbone guiding passages, the first distal segment and the second distal spacing disk;

the structural backbone cross guiding passages are in a left-right crossed arrangement in a horizontal direction, or in an upper-lower crossed arrangement in a vertical direction, so that the second proximal segment structural backbone at the left part of the proximal segment connects with the second distal segment structural backbone at the right part of the second distal segment, and the second proximal segment structural backbone at the right part of the proximal segment connects with the second distal segment structural backbone at the left part of the second distal segment, or the second proximal segment structural backbone at the upper part of the proximal segment connects with the second distal segment structural backbone at the lower part of the second distal segment, and the second proximal segment structural backbone at the lower part of the proximal segment connects with the second distal segment structural backbone at the upper part of the second distal segment.

In a preferred embodiment, the flexible surgical instrument may further include a driving handle including a driving handle base, a gimbal and a linear sliding module; the driving handle base passes through the proximal structural body and connects to one of the two passage fixing plates via the gimbal; the driving handle base connects to the proximal fixing disk via the linear sliding module.

The present invention further provides a flexible surgical instrument with structural backbones in an opposed and crossed arrangement, including a flexible continuous body structure comprising a distal structural body, a proximal structural body and a middle connection body;

the distal structural body includes a first distal segment including a first distal spacing disk, a first distal fixing disk and first distal segment structural backbones, and a second distal segment including a second distal spacing disk, a second distal fixing disk and second distal segment structural backbones; the proximal structural body includes a proximal segment including a proximal spacing disk, a proximal fixing disk, first proximal segment structural backbones and second proximal segment structural backbones;

one end of each the first proximal segment structural backbones on the proximal segment and one end of each the first distal segment structural backbones on the first distal segment are fixedly connected to each other, or each the first proximal segment structural backbones on the proximal segment and corresponding first distal segment structural backbone on the first distal segment is the same structural backbone; one end of each the second proximal segment structural backbones on the proximal segment and one end of each the second distal segment structural backbones on the second distal segment are fixedly connected to each other, or each the second proximal segment structural backbones on the proximal segment and corresponding second distal segment structural backbone on the second distal segment is the same structural backbone;

the middle connection body includes two passage fixing plates, the structural backbone guiding passages and the structural backbone cross guiding passages are fixedly connected between the two passage fixing plates, respectively;

one end of each the first proximal segment structural backbones are fixedly connected to the proximal fixing disk, and the other end thereof are fixedly connected to a first distal fixing disk after passing through the proximal spacing disk, the structural backbone cross guiding passages and the first distal spacing disk in sequence; one end of each the second proximal segment structural backbones are fixedly connected to the proximal fixing plate, and the other end thereof are fixedly connected to the second distal fixing disk after passing through the proximal spacing disk, the structural backbone guiding passages, the first distal segment and the second distal spacing disk in sequence; and The structural backbone cross guiding passages are in an opposed and crossed arrangement about the distribution center.

In a preferred embodiment, the flexible surgical instrument may further includes a driving handle comprising a driving handle base, a gimble and a linear sliding module; the linear sliding module includes a guide bush fixedly provided at a center of the proximal fixing disk and a cylindrical slide slidably connected in the guide bush, one end of the cylindrical slide is fixedly connected to the driving handle base, and the other end thereof is connected to one of the two passage fixing plates via the gimble.

In a preferred embodiment, a surgical end effector is provided at a front distal end of the distal structural body, at least one control wire for the surgical end effector extends through the distal structural body, the other end connects to a surgical end effector driving mechanism provided on the driving handle base.

In a preferred embodiment, the surgical end effector driving mechanism includes a horizontal guide rod, a horizontal moving slider, a link, a vertical guide rod and a vertical moving slider, wherein the vertical guide rod is fixedly connected to the driving handle base and is perpendicular to the axial direction of the driving handle base, the vertical moving slider is slidably connected to the vertical guide rod, the horizontal guide rod is fixedly connected to the driving handle base and is parallel to the axial direction of the driving handle base, the horizontal moving slider is slidably connected to the horizontal guide rod, the horizontal moving slider is located distal to the vertical guide rod, the vertical moving slider connects to the horizontal moving slider via the link; a spring is sleeved on the vertical guide rod, one end of the spring is fixedly connected to the driving handle base, and the other end thereof is fixedly connected to the vertical moving slider; the horizontal moving slider is fixedly connected to one end of the at least one control wire.

In a preferred embodiment, at least one control wire guiding passage is provided between the two passage fixing plates, the at least one control wire extends through the at least one control wire guiding passage.

In a preferred embodiment, the flexible surgical instrument may further include a driving handle cover and a flexible surgical instrument housing; the driving handle cover is fixedly connected to the driving handle base; the middle connection body is located within the flexible surgical instrument housing, the two passage fixing plates are fixedly connected to the flexible surgical instrument housing.

The present invention still further provides a flexible surgical instrument with structural backbones in an opposed and crossed arrangement, the flexible surgical instrument includes a flexible continuum structure comprising a distal structural body, a proximal structure and a middle connection body;

the distal structure includes a first distal segment including a first distal spacing disk, a first distal fixing disk and first distal segment structural backbones, and a second distal segment including a second distal spacing disk, a second distal fixing disk and second distal segment structural backbones; the proximal structure includes a proximal segment including a proximal spacing disk, a proximal fixing disk, first proximal segment structural backbones and second proximal segment structural backbones;

one end of each the first proximal segment structural backbones on the proximal segment and one end of each the first distal segment structural backbones on the first distal segment are fixedly connected to each other, or each the first proximal segment structural backbones on the proximal segment and corresponding first distal segment structural backbone on the first distal segment is the same structural backbone; one end of each the second proximal segment structural backbones on the proximal segment and one end of each the second distal segment structural backbones on the second distal segment are fixedly connected to each other, or each the second proximal segment structural backbones on the proximal segment and corresponding second distal segment structural backbone on the second distal segment is the same structural backbone;

the middle connection body includes two passage fixing plates, the structural backbone guiding passages and the structural backbone cross guiding passages are fixedly connected between the two passage fixing plates, respectively;

one end of each the first proximal segment structural backbones are fixedly connected to the proximal fixing disk, and the other end thereof are fixedly connected to a first distal fixing disk after passing through the proximal spacing disk, the structural backbone guiding passages and the first distal spacing disk in sequence; one end of each the second proximal segment structural backbones are fixedly connected to the proximal fixing disk, and the other end thereof are fixedly connected to the second distal fixing disk after passing through the proximal spacing disk, the structural backbone cross guiding passages, the first distal segment and the second distal spacing disk in sequence; and The structural backbone cross guiding passages are in an opposed and crossed arrangement around a distribution center.

Thanks to the above mentioned technical solutions utilized in the present invention, the present invention has the advantages that 1) The present invention utilizes a continuum structure including a proximal structure, a middle connection body and a distal structure as the main body, wherein the distal structure is associated with the proximal structure via the middle connection body, the proximal structure is associated with the driving handle, thus when the driving handle drives the proximal structure to turn in any direction, the distal structure will turns correspondingly, realizing willful turning movements of the flexible surgical arm. 2) The distal structure, the middle connection body and the proximal structure of the present invention utilize redundant structural backbone arrangement (the number of the structural backbones is greater than three), which improves stability and loading capacity of the system. 3) The present invention is provided with structural backbone cross guiding passages in the middle connection body, so that the first proximal segment structural backbones and the first distal segment structural backbones are in a crossed arrangement in the horizontal (vertical) direction, thereby realizing the effect that when the proximal structure is driven to turn in the horizontal (vertical) direction, the first distal segment correspondingly turns in the same direction, the second distal segment correspondingly turns in an opposite direction; and when the proximal structure is driven to turn in the vertical (horizontal) direction, the first distal segment and the second distal segment both correspondingly turn in an opposite direction. 4) In the present invention, a surgical end effector is provided on a front distal end of the distal structural body, the at least one control wire of the surgical end effector extends through the distal structural body, connects to a surgical end effector driving mechanism located on the driving handle base, thus the surgical end effector may realize control on the action of the surgical end effector by means of pushing and pulling the at least one control wire.

The present invention can be applied in multi-port laparoscopic surgery, as well as in single-port laparoscopic surgery.

DETAILED DESCRIPTION OF THE INVENTION

The present invention will be described in detail in the followings with reference to the drawings and the embodiments.

Embodiment 1

Figure 1:
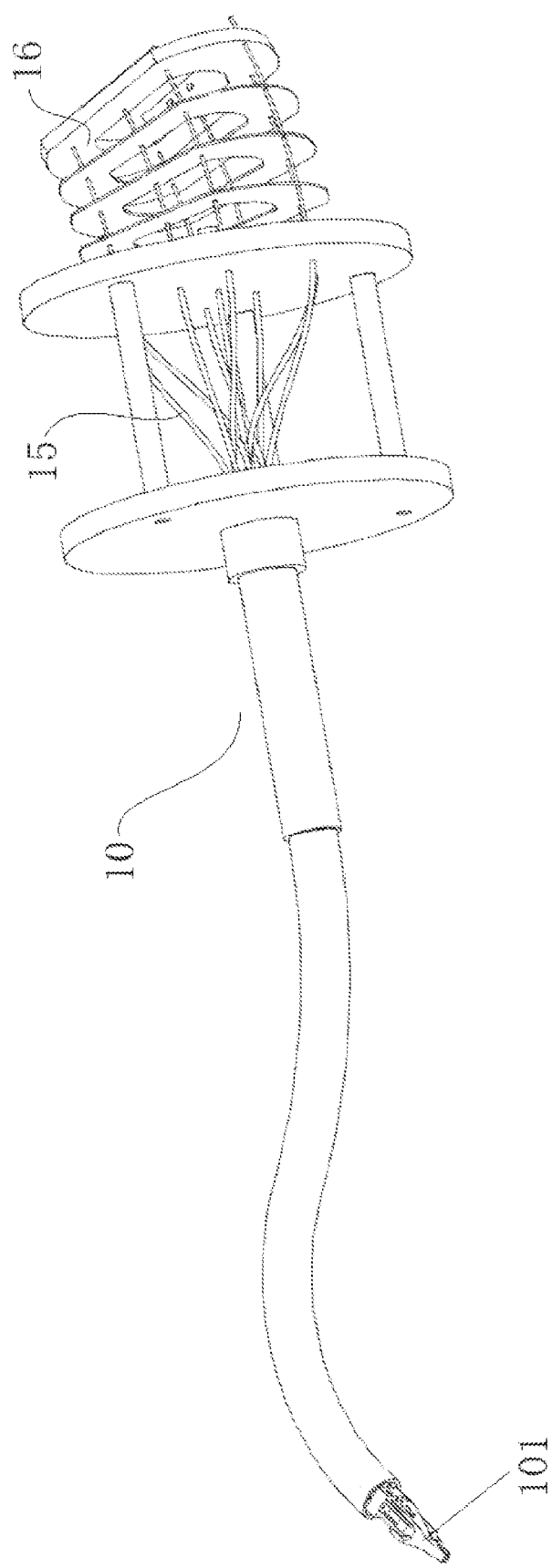
FIG. 1 is a schematic structural illustration of a flexible continuum structure of a flexible surgical instrument according to a first embodiment of the present invention.
Figure 2:
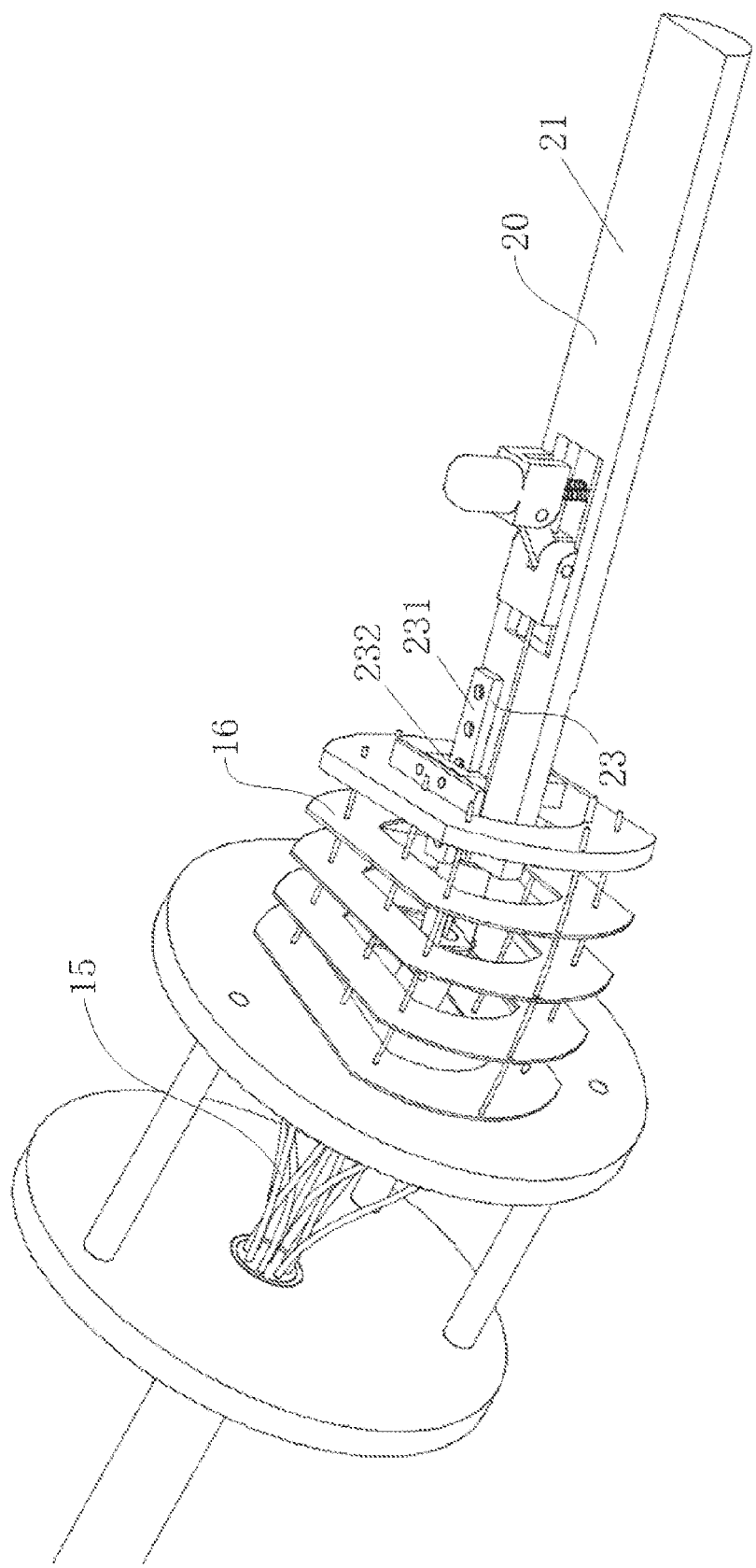
FIG. 2 is a schematic illustration of connection between a driving handle and the flexible continuum structure according to an embodiment of the present invention.

As shown in FIGS. 1, 2, a flexible surgical instrument of the embodiment includes a flexible continuum structure 10 and a driving handle 20.

Figure 3:
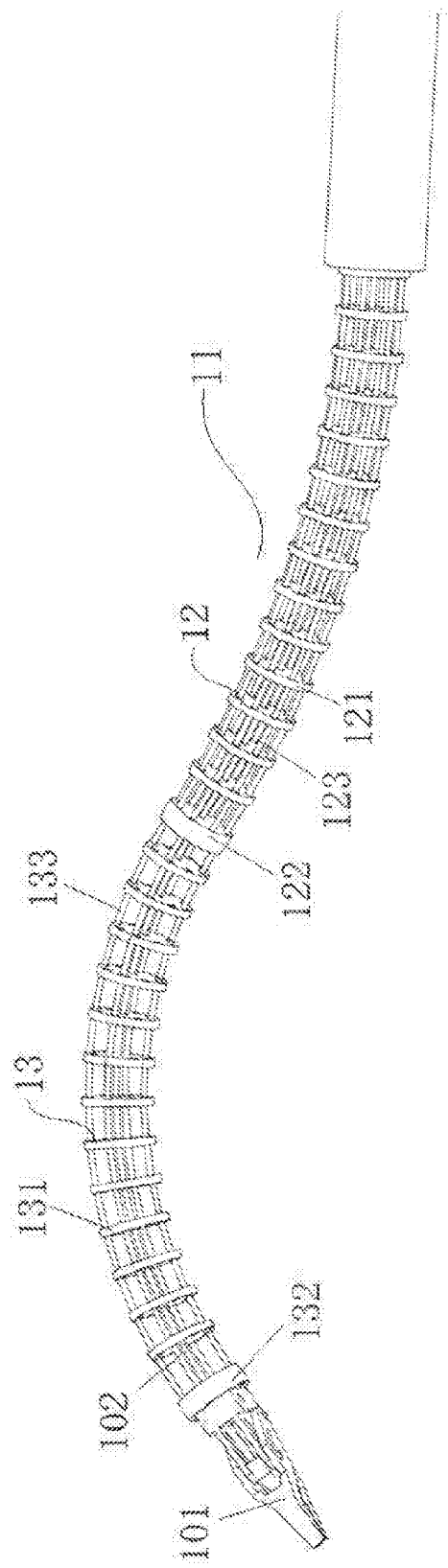
FIG. 3 is a structural schematic illustration of the distal structure of FIG. 1.
Figure 4:
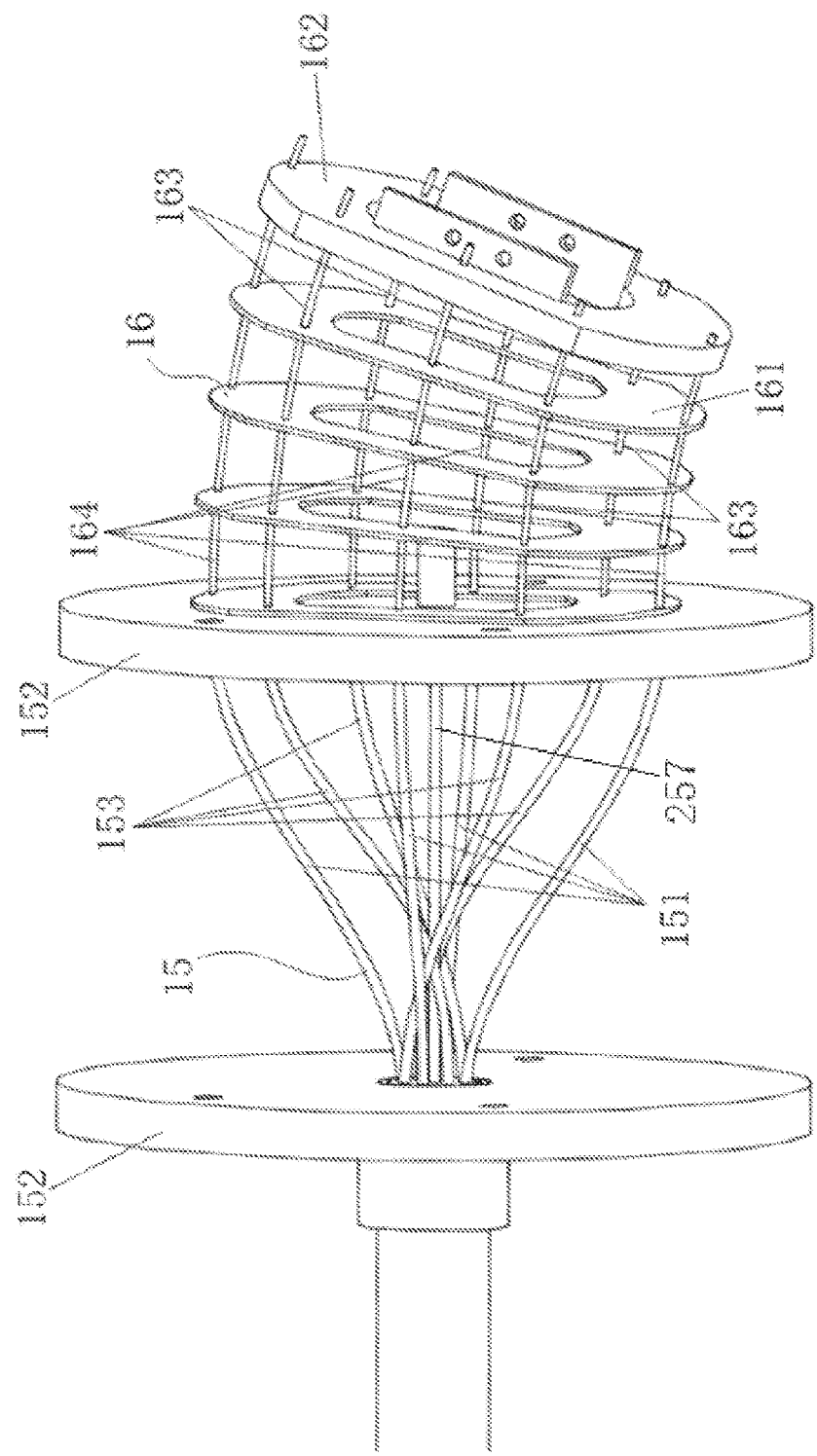
FIG. 4 is a structural schematic illustration of the proximal structure and the middle connection body of FIG. 1.

The flexible continuous body structure 10 includes a distal structural body 11 (as shown in FIG. 3), a proximal structural body 16 (as shown in FIG. 4) and a middle connection body 15. The distal structural body 11 includes a first distal segment 12 and a second distal segment 13 connected in series, the proximal structural body 16 includes a proximal segment. The proximal segment is associated to the first distal segment 12 and the second distal segment 13 by the middle connection body 15, when the proximal structural body 16 turns, the distal structural body 11 may be driven to turn correspondingly. The driving handle 20 is associated to the proximal structural body 16 for controlling turning of the proximal structural body 16.

The first distal segment 12 includes a first distal spacing disk 121, a first distal fixing disk 122 and first distal segment structural backbones 123; the second distal segment 13 includes a second distal spacing disk 131, a second distal fixing disk 132 and second distal segment structural backbones 133. Wherein, the first distal spacing disk 121 and the second distal spacing disk 131 are respectively spaced distributed within the first distal segment 12 and the second distal segment 13, which function to prevent the first distal segment structural backbones 123 and the second distal segment structural backbones 133 from being unstable when being pushed.

The proximal segment includes a proximal spacing disk 161, a proximal fixing disk 162, first proximal segment structural backbones 163 and second proximal segment structural backbones 164. Wherein, the proximal spacing disk 161 is spaced distributed within the proximal segment, which functions to prevent the first proximal segment structural backbones 163 and the second proximal segment structural backbones 164 from being unstable when being pushed.

one end of each the first proximal segment structural backbones 163 on the proximal segment and one end of each the first distal segment structural backbones 123 on the first distal segment 12 are fixedly connected to each other, or each the first proximal segment structural backbones 163 on the proximal segment and corresponding first distal segment structural backbone 123 on the first distal segment 12 is the same structural backbone;

one end of each the second proximal segment structural backbones 164 on the proximal segment and the second distal segment structural backbones 133 on the second distal segment 13 are fixedly connected to each other, or each the second proximal segment structural backbones 164 on the proximal segment and corresponding second distal segment structural backbone 133 on the second distal segment 13 is the same structural backbone.

The number of the first distal segment structural backbones 123 on the first distal segment 12 and the number of the second distal segment structural backbones 133 on the second distal segment 13 are both more than three.

The middle connection body 15 includes two passage fixing plates 152, structural backbone guiding passages 151 and structural backbone cross guiding passages 153 fixedly connected between the two passage fixing plates 152 respectively. One end of each the first proximal segment structural backbones 163 are fixedly connected to the proximal fixing disk 162, the other end thereof are fixedly connected to the first distal fixing disk 122 after extending through the proximal spacing disk 161, the structural backbone cross guiding passages 153 and the first distal spacing disk 121 in sequence; one end of each the second segment structural backbones 164 are fixedly connected to the proximal fixing disk 162, the other end thereof are fixedly connected to the second distal fixing disk 132 after extending through the proximal spacing disk 161, the structural backbone guiding passages 151, the first distal segment 12 and the second distal spacing disk 131 in sequence. The structural backbone guiding passages 151 and the structural backbone cross guiding passages 153 function to remain the shape of the structural backbones unchanged when the structural backbones is pushed, pulled.

Wherein, the structural backbone cross guiding passages 153 are in a left-right crossed arrangement in a horizontal direction or in an upper-lower crossed arrangement in a vertical direction, so that the first proximal segment structural backbone 163 at a left part of the proximal segment connects to a first distal segment structural backbone 123 at a right part of the first distal segment 12, and the first proximal segment structural backbone 163 at a right part of the proximal segment connects to the first distal segment structural backbone 123 at the left part of the first distal segment 12; or the first proximal segment structural backbone 163 at an upper part of the proximal segment connects to a first distal segment structural backbone 123 at a lower part of the first distal segment 12, and the first proximal segment structural backbone 163 at a lower part of the proximal segment connects to the first distal segment structural backbone 123 at an upper part of the first distal segment 12.

When the structural backbone cross guide passages 153 is in a crossed arrangement in horizontal direction, if the proximal structural body 16 turns along the horizontal direction, the first distal segment 12 will turn in the same direction along the horizontal direction with a certain proportion (determined collectively by a distance in horizontal direction between the first proximal segment structural backbones 163 at the left and right parts of the proximal segment and a distance in horizontal direction between the first distal segment structural backbones 123 at the left and right parts of the first distal segment 12), the second distal segment 13 will turn in an opposite direction along the horizontal direction with a certain proportion (determined collectively by a distance in horizontal direction between the second proximal segment structural backbones 164 at the left and right parts of the proximal segment and a distance in horizontal direction between the second distal segment structural backbones 133 at the left and right parts of the second distal segment 13); if the proximal structural body 16 turns along the vertical direction, the first distal segment 12 will turn in an opposite direction along the vertical direction with a certain proportion (determined collectively by a distance in vertical direction between the first proximal segment structural backbones 163 at the upper and lower parts of the proximal segment and a distance in vertical direction between the first distal segment structural backbones 123 at the upper and lower parts of the first distal segment 12), the second distal segment 13 will turn in an opposite direction along the vertical direction with a certain proportion (determined collectively by a distance in vertical direction between the second distal segment structural backbones 164 at the upper and lower parts of the proximal segment and a distance in vertical direction between the second distal segment structural backbones 133 at the upper and lower parts of the second distal segment 13).

When the structural backbone cross guide passages 153 is in a crossed arrangement in vertical direction, if the proximal structural body 16 turns along the horizontal direction, the first distal segment 12 will turn in an opposite direction along the horizontal direction with a certain proportion (determined collectively by a distance in horizontal direction between the first proximal segment structural backbones 163 at the left and right parts of the proximal segment and a distance in horizontal direction between the first distal segment structural backbones 123 at the left and right parts of the first distal segment 12), the second distal segment 13 will turn in an opposite direction along the horizontal direction with a certain proportion (determined collectively by a distance in horizontal direction between the second proximal segment structural backbones 164 at the left and right parts of the proximal segment and a distance in horizontal direction between the second distal segment structural backbones 133 at the left and right parts of the second distal segment 13); if the proximal structure 16 turns along the vertical direction, the first distal segment 12 will turn in the same direction along the vertical direction with a certain proportion (determined collectively by a distance in vertical direction between the first proximal segment structural backbones 163 at the upper and lower parts of the proximal segment and a distance in vertical direction between the first distal segment structural backbones 123 at the upper and lower parts of the first distal segment 12), the second distal segment 13 will turn in an opposite direction along the vertical direction with a certain proportion (determined collectively by a distance in vertical direction between the second proximal segment structural backbones 164 at the upper and lower parts of the proximal segment and a distance in vertical direction between the second distal segment structural backbones 133 at the upper and lower parts of the second distal segment 13).

Figure 5:
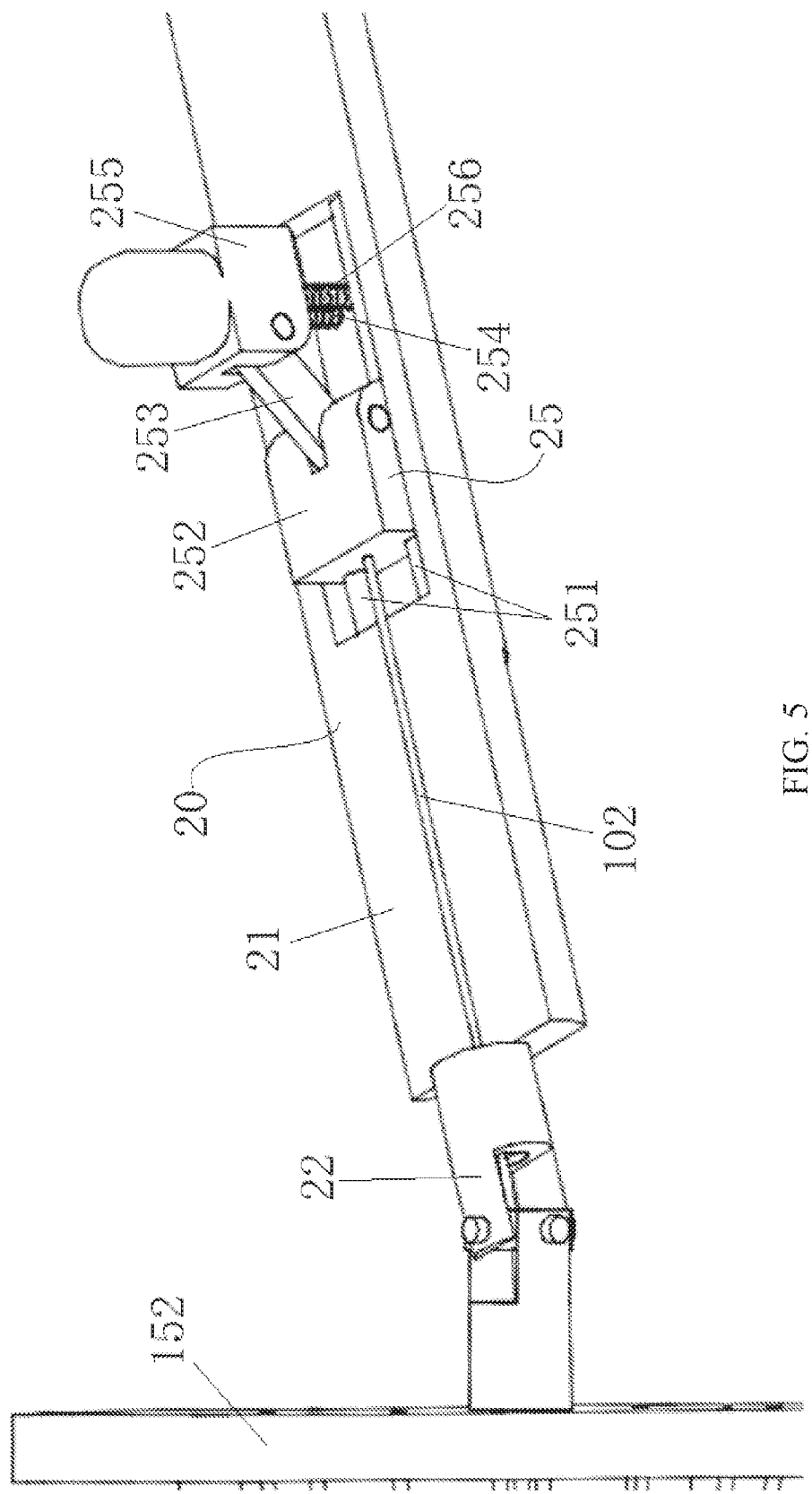
FIG. 5 is a structural schematic illustration of a driving handle according to an embodiment of the present invention.

As shown in FIGS. 2, 5, the driving handle 20 includes a driving handle base 21, a gimble 22 and a linear sliding module 23. Wherein, the driving handle base 21 extends through the proximal structure 16, and connects to one of the two passage fixing plates 152 via the gimble 22, so that the driving handle base 21 is able to rotate towards any direction about a fixing point. The driving handle base 21 connects to the proximal fixing disk 162 via the linear sliding module 23, the linear sliding module 23 includes a track 231 and a slide 232 slidably connected on the track 231, wherein the track 231 is fixedly connected on the driving handle base 21, and the slide 232 connects with the proximal fixing disk 162. The linear sliding module 23 functions to allow a central axis of the proximal fixing disk 162 to be always coincide with a central axis of the driving handle 20, and enable the driving handle 20 to slide along the central axis of the proximal fixing disk 162, thus guaranteeing that when the driving handle 20 controls the proximal structural body 16 to turn, its shape of turning is approximately a circular arc.

Further, a surgical end effector 101 is provided at a distal end of the distal structural body 11, at least one control wire 102 for the surgical end effector 101 extends through the distal structural body 11, and the other end thereof connects to a surgical end effector driving mechanism 25 provided on the driving handle base 21. The surgical end effector driving mechanism 25 includes a horizontal guide rod 251, a horizontal moving slider 252, a link 253, a vertical guide rod 254 and a vertical moving slider 255, wherein the vertical guide rod 254 is fixedly connected to the driving handle base 21 and is perpendicular to the axial direction of the driving handle base 21; the vertical moving slider 255 is slidably connected on the vertical guide rod 254; there are two horizontal guide rods 251 fixedly connected to the driving handle base 21 and distributed on two sides of the vertical guide rod 254, the horizontal guide rods 251 are parallel to the axial direction of the driving handle base 21. The two horizontal guide rods 251 together slidably support the horizontal moving slider 252, the horizontal moving slider 252 is located in front of the vertical guide rod 254. The vertical moving slider 255 connects to the horizontal moving slider 252 via the link 253. A spring 256 is sleeved on the vertical guide rod 254, one end of the spring 256 is fixedly connected to the driving handle base 21, and the other end thereof is fixedly connected to the vertical moving slider 255. The horizontal moving slider 252 is fixedly connected to the control wire 102. When the vertical moving slider 255 is pressed down, the vertical moving slider 255 urges the horizontal moving slider 252 via the link 253 to move the horizontal moving slider forwardly along the horizontal guide rod 251, thus creating a push force on the control wire 102, so as to drive the surgical end effector 101 (such as surgical forceps) to act. The control wire 102 of the surgical end effector 101 can also transfer various kind of energy, such as electricity, high frequency vibration and the like, to execute electrical surgery.

Further, at least one control wire guiding passage 257 is also provided between the passage fixing plates 152, the control wire 102 extends through the control wire guiding passage 257, the control wire guiding passage 257 functions to prevent the control wire 102 from being unstable when being pushed.

Figure 6:
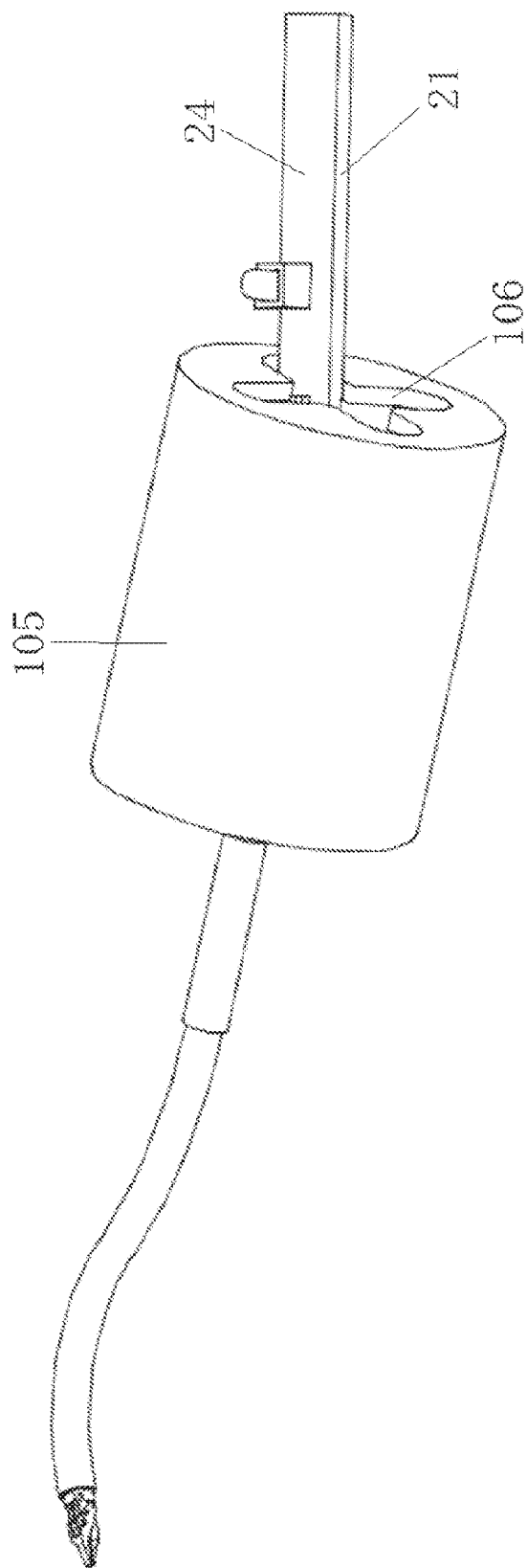
FIG. 6 is a structural schematic illustration of the flexible surgical instrument according to the first embodiment of the present invention, after the surgical instrument is mounted with a flexible surgical instrument housing.
Figure 7:
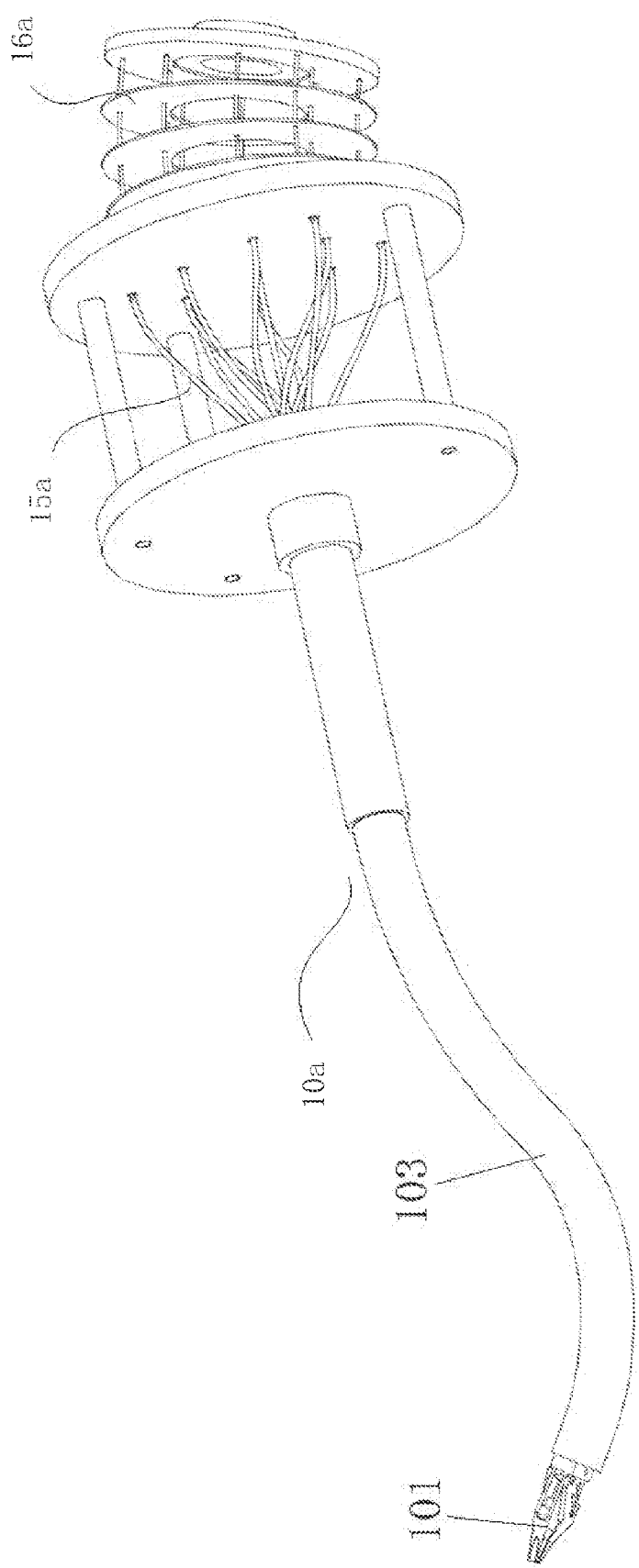
FIG. 7 is a schematic structural illustration of a flexible continuum structure of a flexible surgical instrument according to a second embodiment of the present invention.

Further, as shown in FIG. 6, the present invention also includes a driving handle cover 24 and a flexible surgical instrument housing 105. Wherein, the driving handle cover 24 is fixedly connected to the driving handle base 21 to form an enclosed handle profile. The middle connections body 15 and the proximal structural body 16 are both located within the flexible surgical instrument housing 105, the passage fixing plate 152 is fixedly connected to the flexible surgical instrument housing 105. A cross-shaped chute 106 is provided at a proximal end of the flexible surgical instrument housing 105, the driving handle 20 is rotatable along the chute 106, i.e. rotate in the horizontal direction and in the vertical direction, respectively. Besides, when the driving handle 20 is rotated, the rotation movement can be transferred to the passage fixing plate 152 via the gimble 22, thus in turn rotates the whole flexible surgical instrument, realizing control on a rolling angle of the surgical end effector 101. Further, the chute 105 of the present invention can also be designed as various shapes according to various moving requirements.

Embodiment 2

This embodiment differs from Embodiment 1 in that the first proximal segment structural backbones 163 extends through the structural backbone guiding passages 151, and the second proximal segment structural backbones 164 extends through the structural backbone cross guiding passages 153. The structures of the rest portion are identical to those in Embodiment 1.

Embodiment 3

As shown in FIGS. 7-11, this embodiment includes a flexible continuum structure 10a and a driving handle 20.

Figure 9:
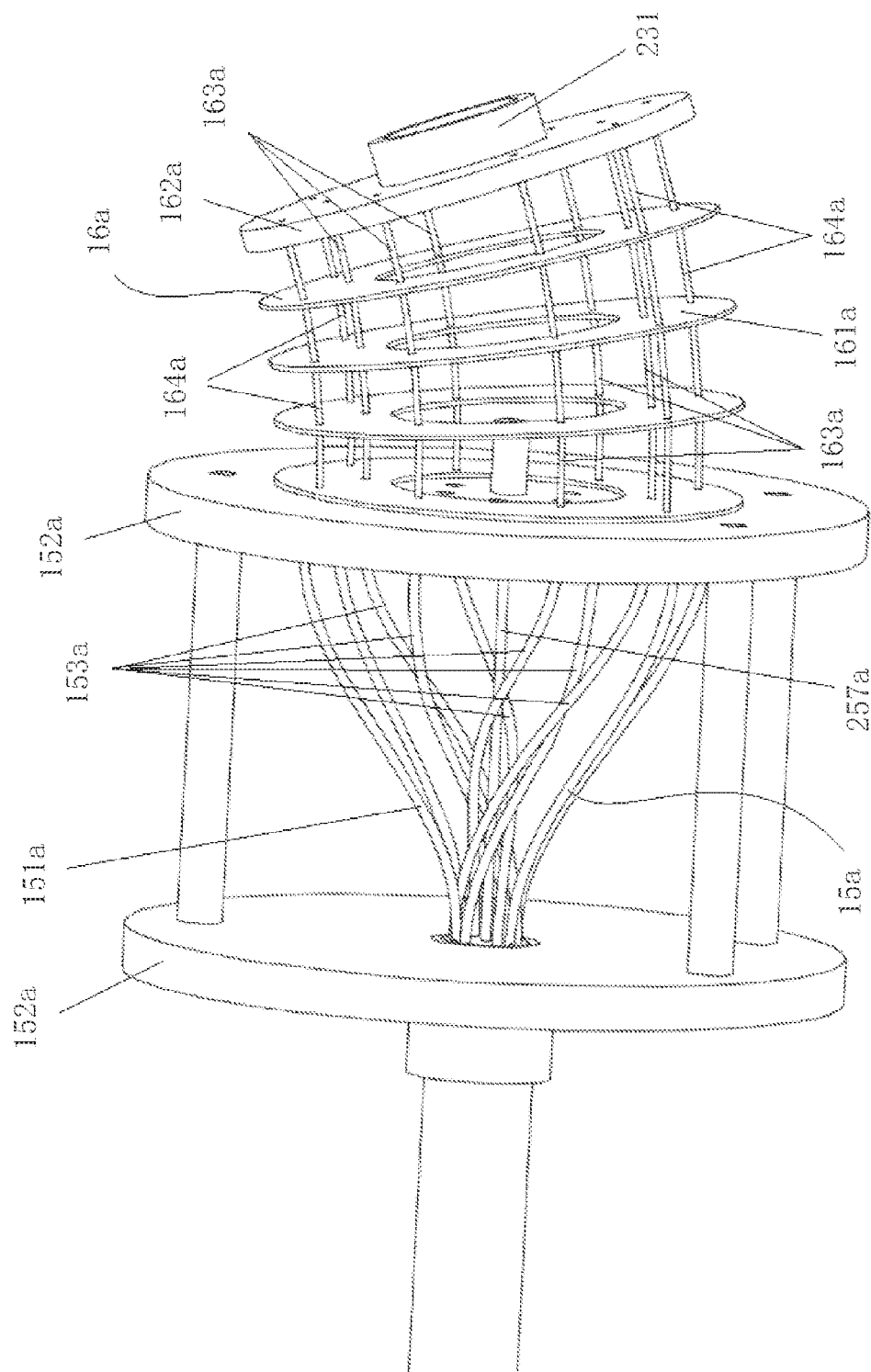
FIG. 9 is a structural schematic illustration of the proximal structure and the middle connection body of an embodiment of the present invention.
Figure 10:
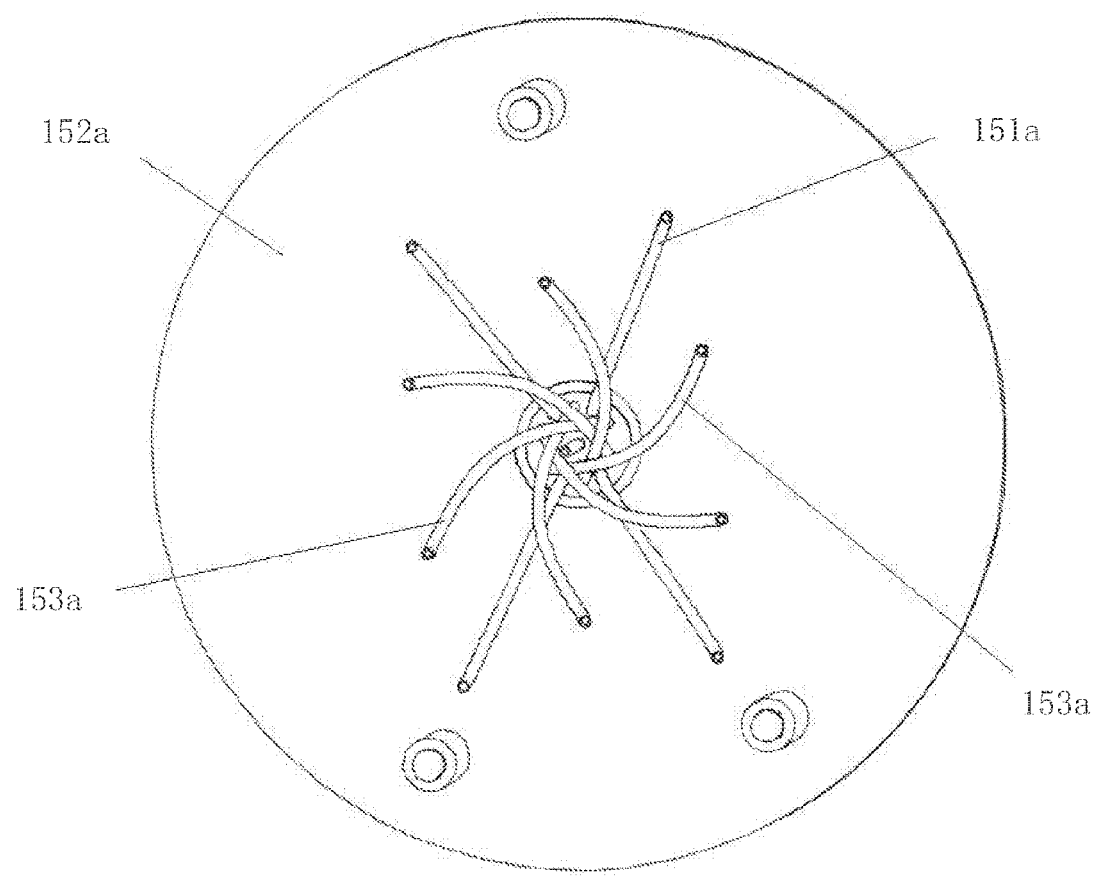
FIG. 10 is a structural schematic illustration of the middle connection body of FIG. 9.

The flexible continuum structure 10 includes a distal structure 11 (can be identical to the preceding embodiments, see FIG. 3), a proximal structural body 16a (as shown in FIG. 9) and a middle connection body 15a. The distal structural body 11 includes a first distal segment 12 and a second distal segment 13 connected in series, the proximal structural body 16a includes a proximal segment. The proximal segment is associated to the first distal segment 12 and the second distal segment 13 by the middle connection body 15a, when the proximal structural body 16a turns, the distal structural body 11 may be driven to turn correspondingly. The driving handle 20a is associated to the proximal structural body 16a for controlling turning of the proximal structural body 16a.

The first distal segment 12 includes a first distal spacing disk 121, a first distal fixing disk 122 and first distal segment structural backbones 123; the second distal segment 13 includes a second distal spacing disk 131, a second distal fixing disk 132 and second distal segment structural backbones 132. Wherein, the first distal spacing disk 121 and the second distal spacing disk 131 are respectively spaced distributed within the first distal segment 12 and the second distal segment 13, which function to prevent the first distal segment structural backbones 123 and the second distal segment structural backbones 133 from being unstable when being pushed.

The proximal segment includes a proximal spacing disk 161a, a proximal fixing disk 162a, first proximal segment structural backbones 163a and second proximal segment structural backbones 164a. Wherein, the proximal spacing disk 161a is spaced distributed within the proximal segment, which functions to prevent the first proximal segment structural backbones 163a and the second proximal segment structural backbones 164a from being unstable when being pushed.

One end of each the first proximal segment structural backbones 163a on the proximal segment and one end of each the first distal structural backbones 123 on the first distal segment 12 are fixedly connected to each other, or or each the first proximal segment structural backbones 163a on the proximal segment and corresponding first distal segment structural backbone 123 on the first distal segment 12 is the same structural backbone;

the second proximal segment structural backbones 164a on the proximal segment and the second structural backbones 133 on the second distal segment 13 are fixedly connected to each other, or each the second proximal segment structural backbones 164a on the proximal segment and corresponding second distal segment structural backbone 133 on the second distal segment 13 is the same structural backbone.

The number of the first distal segment structural backbones 123 on the first distal segment 12 and the number of the second distal segment structural backbones 133 on the second distal segment 13 are both more than three.

The middle connection body 15a includes two passage fixing plates 152a, structural backbone guiding passages 151a and structural backbone cross guiding passages 153a fixedly connected between the two passage fixing plates 152a. One end of each first proximal segment structural backbones 163a are fixedly connected to the proximal fixing disk 162a, the other end thereof are fixedly connected to the first distal fixing disk 122 after extending through the proximal spacing disk 161a, the structural backbone cross guiding passages 153a and the first distal spacing disk 121 in sequence; one end of each the second proximal segment backbones 164a are fixedly connected to the proximal fixing disk 162a, the other end thereof are fixedly connected to the second distal fixing disk 132 after extending through the proximal spacing disk 161a, the structural backbone guiding passages 151a, the first distal segment 12 and the second distal spacing disk 131 in sequence. The structural backbone guiding passages 151a and the structural backbone cross guiding passages 153a function to remain the shape of the structural backbones unchanged when the structural backbones is pushed, pulled. Wherein, the structural backbone cross guiding passages 153a are distributed in central symmetry (as shown in FIG. 9), and the structural backbone cross guiding passages 153a are arranged in an opposed crossed arrangement around the distribution center, so that the first proximal segment structural backbone 163a at one part of the proximal segment connects to the first distal segment structural backbone 123 at one part of the first distal segment 12, thus realizing that when the proximal structural body 16 is driven to turn in any direction, the first distal segment 12 turns in the same direction correspondingly.

The structural backbone guiding passages 153a of this embodiment is arranged in an opposed crossed arrangement around the distribution center, when the proximal structural body 16a turns in a certain direction, the first distal segment 12 will turn in the same direction with a certain proportion (the proportion is determined collectively by a distribution radius of the first proximal segment structural backbones 163a in the proximal segment and a distribution radius of the first distal segment structural backbones 123 in the first distal segment 12), and the second distal segment 13 will turn in an opposite direction with a certain proportion (the proportion is determined collectively by a distribution radius of the second proximal segment structural backbones 164a in the proximal segment and a distribution radius of the second distal segment structural backbones 133 in the second distal segment 13).

Figure 8:
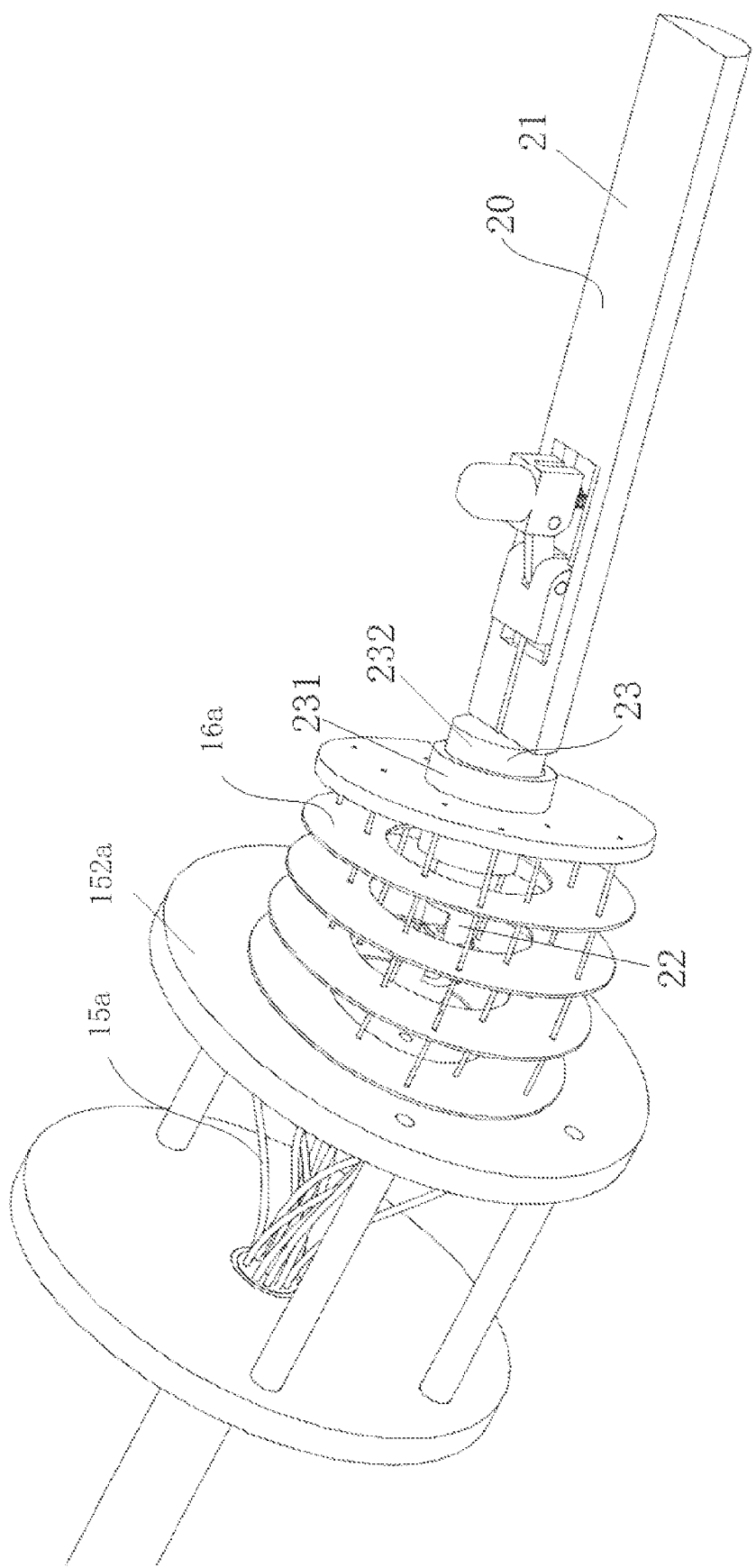
FIG. 8 is a schematic illustration of connection between a driving handle and the flexible continuum structure according to another embodiment of the present invention.

As shown in FIGS. 5, 8, the driving handle 20 includes a driving handle base 21, a gimble 22 and a linear sliding module 23. Wherein, the driving handle base 21 is connected to the proximal fixing disk 162a via the linear sliding module 23, the linear sliding module 23 includes a guide bush 231 fixedly provided at a center of the proximal fixing disk 162a and a cylindrical slider 232 slidably connected in the guide bush 231. One end of the cylindrical slider 232 is fixedly connected to the driving handle base 21, the other end thereof is connected to one of the two passage fixing plates 152a via the gimble 22, so that the driving handle base 21; the vertical moving slider 255 is slidably connected on the vertical guide rod 254; there are two horizontal guide rods 251 fixedly connected to the driving handle base 21 and distributed on two sides of the vertical guide rod 254, the horizontal guide rods 251 are parallel to the axial direction of the driving handle base 21. The two horizontal guide rods 251 together slidably support the horizontal moving slider 252, the horizontal moving slider 252 is located in front of the vertical guide rod 254. The vertical moving slider 255 connects to the horizontal moving slider 252 via the link 253. A spring 256 is sleeved on the vertical guide rod 254, one end of the spring 256 is fixedly connected to the driving handle base 21, and the other end thereof is fixedly connected to the vertical moving slider 255. The horizontal moving slider 252 is fixedly connected to the control wire 102. When the vertical moving slider 255 is pressed down, the vertical moving slider 255 urges the horizontal moving slider 252 via the link 253 to move the horizontal moving slider forwardly along the horizontal guide rod 251, thus creating a push force on the control wire 102, so as to drive the surgical end effector 101 (such as surgical forceps) to act. The control wire 102 of the surgical end effector 101 can also transfer various kind of energy, such as electricity, high frequency vibration and the like, to execute electrical surgery.

21; the vertical moving slider 255 is slidably connected on the vertical guide rod 254; there are two horizontal guide rods 251 fixedly connected to the driving handle base 21 and distributed on two sides of the vertical guide rod 254, the horizontal guide rods 251 are parallel to the axial direction of the driving handle base 21. The two horizontal guide rods 251 together slidably support the horizontal moving slider 252, the horizontal moving slider 252 is located in front of the vertical guide rod 254. The vertical moving slider 255 connects to the horizontal moving slider 252 via the link 253. A spring 256 is sleeved on the vertical guide rod 254, one end of the spring 256 is fixedly connected to the driving handle base 21, and the other end thereof is fixedly connected to the vertical moving slider 255. The horizontal moving slider 252 is fixedly connected to the control wire(s) 102. When the vertical moving slider 255 is pressed down, the vertical moving slider 255 urges the horizontal moving slider 252 via the link 253 to move the horizontal moving slider forwardly along the horizontal guide rod 251, thus creating a push force on the control wire(s) 102, so as to drive the surgical end effector 101 (such as surgical forceps) to act. The control wire(s) 102 of the surgical end effector 101 can also transfer various kind of energy, such as electricity, high frequency vibration and the like, to execute electrical surgery.

Further, as shown in FIG. 9, at least one control wire guiding passage 257a is also provided between the passage fixing plates 152a, the control wire 102 extends through the control wire guiding passage 257a, the control wire guiding passage 257a functions to prevent the control wire 102 from being unstable when being pushed.

Figure 11:
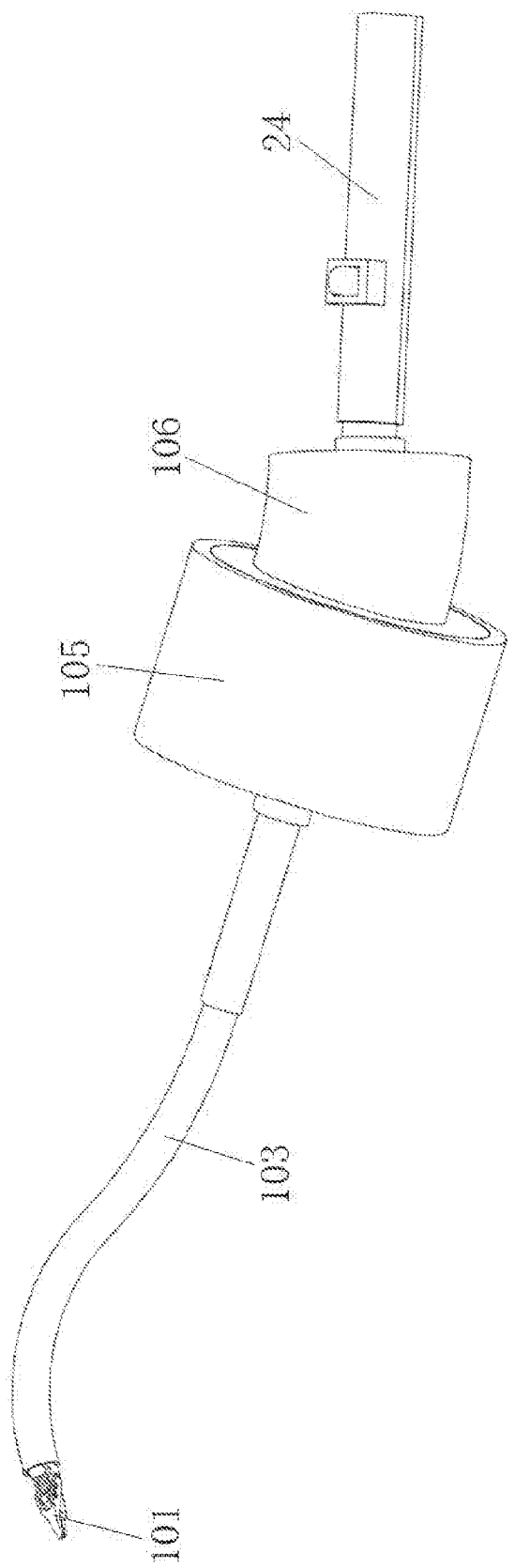
FIG. 11 is a structural schematic illustration of the flexible surgical instrument according to the present invention, after the surgical instrument is mounted with a flexible surgical instrument housing.

Further, as shown in FIG. 11, the present invention also includes a driving handle cover 24 and a flexible surgical instrument housing 105. Wherein, the driving handle cover 24 is fixedly connected to the driving handle base 21 to form an enclosed handle profile. The middle connections body 15a is located within the flexible surgical instrument housing 105, the passage fixing plates 152a are fixedly connected to the flexible surgical instrument housing 105. Besides, when the driving handle 20 is rotated, the rotation movement can be transferred to the two passage fixing plates 152a via the gimble 22, thus in turn rotates the whole flexible surgical instrument, realizing control on a rolling angle of the surgical end effector 101.

Further, as shown in FIG. 11, a proximal structural body skin 106 covers outside the proximal structural body 16, a skin 103 covers outside the distal structural body 11. The skins 103, 106 functions to improve appearance, and can improve surface smoothness of the distal structural body 11.

Embodiment 4

This embodiment differs from Embodiment 1 in that the first proximal segment structural backbones 163a extends through the structural backbone guiding passage 151a, and the second proximal segment structural backbones 164a extends through the structural backbone cross guiding passages 153a. The structures of the rest portion are identical to those in Embodiment 1.

The present invention is described only by the above embodiments, the structure, providing position and connection of the parts can be varied. Based on the technical solutions of the present invention, the modification or equivalent variations on the individual parts based on the principle of the present invention shall not be excluded from the protective scope of the present invention.

The invention claimed is:

1. A flexible surgical instrument with structural backbones in a crossed arrangement, wherein said flexible surgical instrument includes a flexible continuous body structure comprising a distal structural body, a proximal structural body, and a middle connection body;
    said distal structural body includes a first distal segment including a first distal spacing disk, a first distal fixing disk, and first distal segment structural backbones, and a second distal segment including a second distal spacing disk, a second distal fixing disk, and second distal segment structural backbones; said proximal structural body includes a proximal segment including a proximal spacing disk, a proximal fixing disk, first proximal segment structural backbones and second proximal segment structural backbones;
    one end of each said first proximal segment structural backbones on said proximal segment and one end of each said first distal segment structural backbones on said first distal segment are fixedly connected to each other, or each said first proximal segment structural backbones on said proximal segment and corresponding first distal segment structural backbone on said first distal segment is the same structural backbone; one end of each said second proximal segment structural backbones on said proximal segment and one end of each said second distal segment structural backbones on said second distal segment are fixedly connected to each other, or each of the second proximal segment structural backbones on said proximal segment and corresponding second distal segment structural backbone on said second distal segment is the same structural backbone;
    said middle connection body includes two passage fixing plates, structural backbone guiding passages and structural backbone cross guiding passages are fixedly connected between the two passage fixing plates, respectively;
    one end of each said first proximal segment structural backbones are fixedly connected to said proximal fixing disk, and the other end thereof are fixedly connected to said first distal fixing disk after passing through said proximal spacing disk, said structural backbone cross guiding passages and said first distal spacing disk in sequence; one end of each said second proximal segment structural backbones are fixedly connected to said proximal fixing disk, and the other end thereof are fixedly connected to said second distal fixing disk after passing through said proximal spacing disk, said structural backbone guiding passages, said first distal segment and said second distal spacing disk in sequence; and
    said structural backbone cross guiding passages are in a left-right crossed arrangement in a horizontal direction or in an upper-lower crossed arrangement in a vertical direction, so that one end of said first proximal segment structural backbone at a left part of said proximal segment connects to one end of said first distal segment structural backbone at a right part of said first distal segment, and one end of said first proximal segment structural backbone at a right part of said proximal segment connects to one end of said first distal segment structural backbone at a left part of said first distal segment; or one end of said first proximal segment structural backbone at an upper part of said proximal segment connects to one end of said first distal segment structural backbone at a lower part of said first distal segment, and one end of said first proximal segment structural backbone at a lower part of said proximal segment connects to one end of said first distal segment structural backbone at an upper part of said first distal segment.

2. The flexible surgical instrument with structural backbones in a crossed arrangement according to claim 1, wherein said flexible surgical instrument further includes a driving handle comprising a driving handle base, a gimble, and a linear sliding module; said driving handle base extends through said proximal structural body and connects to one of said two passage fixing plates via said gimble; and said driving handle base is connected to said proximal fixing disk via said linear sliding module.

3. The flexible surgical instrument with structural backbones in a crossed arrangement according to claim 2, wherein said linear sliding module includes a track and a slider slidably connected on said track, said track is fixedly connected on said driving handle base, said slider is fixedly connected to said proximal fixing disk.

4. The flexible surgical instrument with structural backbones in a crossed arrangement according to claim 2, wherein a surgical end effector is provided at a distal end of said distal structural body, at least one control wire for said surgical end effector extending through said distal structural body and connecting to a surgical end effector driving mechanism provided on said driving handle base.

5. The flexible surgical instrument with structural backbones in a crossed arrangement according to claim 4, wherein said surgical end effector driving mechanism includes a horizontal guide rod, a horizontal moving slider, a link, a vertical guide rod, and a vertical moving slider, wherein said vertical guide rod is fixedly connected to said driving handle base and is perpendicular to the axial direction of said driving handle base, said vertical moving slider is slidably connected to said vertical guide rod, said horizontal guide rod is fixedly connected to said driving handle base and is parallel to the axial direction of said driving handle base, said horizontal moving slider is slidably connected to said horizontal guide rod, said horizontal moving slider is located distal to said vertical guide rod, said vertical moving slider connects to said horizontal moving slider via said link; a spring is sleeved on said vertical guide rod, one end of said spring is fixedly connected to said driving handle base, and the other end thereof is fixedly connected to said vertical moving slider; said horizontal moving slider is fixedly connected to one end of said at least one control wire.

6. The flexible surgical instrument with structural backbones in a crossed arrangement according to claim 4, wherein at least one control wire guiding passage is provided between said two passage fixing plates, and said at least one control wire extends through said at least one control wire guiding passage.

7. The flexible surgical instrument with structural backbones in a crossed arrangement according to claim 2, wherein said flexible surgical instruction further comprises a driving handle cover and a flexible surgical instrument housing; said driving handle cover is fixedly connected to said driving handle base; said middle connection body and said proximal structural body are both located within said flexible surgical instrument housing, said two passage fixing plates are fixedly connected to said flexible surgical instrument housing; and a chute for rotation of said driving handle is provided at a proximal end of said flexible surgical instrument housing.

8. The flexible surgical instrument with structural backbones in a crossed arrangement according to claim 7, wherein said chute is of a cross shape.

9. The flexible surgical instrument with structural backbones in an opposed crossed arrangement according to claim 1, wherein said flexible surgical instrument further includes a driving handle comprising a driving handle base, a gimble and a linear sliding module; said linear sliding module includes a guide bush fixedly provided at a center of said proximal fixing disk and a cylindrical slider slidably connected in said guide bush, one end of said cylindrical slider is fixedly connected to said driving handle base, and the other end thereof is connected to one of said two passage fixing plates via said gimble.

10. The flexible surgical instrument with structural backbones in an opposed crossed arrangement according to claim 9, wherein a surgical end effector is provided at a distal end of said distal structural body, at least one control wire for said surgical end effector extends through said distal structural body, the other end thereof connects to a surgical end effector driving mechanism provided on said driving handle base.

11. The flexible surgical instrument with structural backbones in an opposed crossed arrangement according to claim 10, wherein said surgical end effector driving mechanism includes a horizontal guide rod, a horizontal moving slider, a link, a vertical guide rod, and a vertical moving slider, wherein said vertical guide rod is fixedly connected to said driving handle base and is perpendicular to the axial direction of said driving handle base, said vertical moving slider is slidably connected to said vertical guide rod, said horizontal guide rod is fixedly connected to said driving handle base and is parallel to the axial direction of said driving handle base, said horizontal moving slider is slidably connected to said horizontal guide rod, said horizontal moving slider is located distal to said vertical guide rod, said vertical moving slider connects to said horizontal moving slider via said link; a spring is sleeved on said vertical guide rod, one end of said spring is fixedly connected to said driving handle base, and the other end thereof is fixedly connected to said vertical moving slider; and said horizontal moving slider is fixedly connected to one end of said at least one control wire.

12. The flexible surgical instrument with structural backbones in an opposed crossed arrangement according to claim 10, wherein at least one control wire guiding passages is provided between said two passage fixing plates, said at least one control wire extends through said at least one control wire guiding passage.

13. The flexible surgical instrument with structural backbones in an opposed crossed arrangement according to claim 9, wherein said flexible surgical instrument further includes a driving handle cover and a flexible surgical instrument housing; said driving handle cover is fixedly connected to said driving handle base; said middle connection body is located within said flexible surgical instrument housing, said two passage fixing plates are fixedly connected to said flexible surgical instrument housing.

14. A flexible surgical instrument with structural backbones in a crossed arrangement, wherein said flexible surgical instrument includes a flexible continuous body structure comprising a distal structural body, a proximal structural body and a middle connection body;

said distal structural body includes a first distal segment including a first distal spacing disk, a first distal fixing disk and first distal segment structural backbones, and a second distal segment including a second distal spacing disk, a second distal fixing disk, and second distal segment structural backbones; said proximal structural body includes a proximal segment including a proximal spacing disk, a proximal fixing disk, first proximal segment structural backbones, and second proximal segment structural backbones;

one end of each said first proximal segment structural backbones on said proximal segment and one end of each said first distal segment structural backbones on said first distal segment are fixedly connected to each other, or each said first proximal segment structural backbones on said proximal segment and corresponding first distal segment structural backbone on said first distal segment is the same structural backbone; one end of each said second proximal segment structural backbones on said proximal segment and one end of each said second distal segment structural backbones on said second distal segment are fixedly connected to each other, or each of the second proximal segment structural backbones on said proximal segment and corresponding second distal segment structural backbone on said second distal segment is the same structural backbone;

said middle connection body includes two passage fixing plates, structural backbone guiding passages and structural backbone cross guiding passages are fixedly connected between the two passage fixing plates, respectively;

one end of said first proximal segment structural backbones is fixedly connected to said proximal fixing disk, and the other end thereof is fixedly connected to said first distal fixing disk after passing through said proximal spacing disk, said structural backbone guiding passages and said first distal spacing disk in sequence;

one end of each said second proximal segment structural backbones are fixedly connected to said proximal fixing disk, and the other end thereof are fixedly connected to said second distal fixing disk after passing through said proximal spacing disk, said structural backbone cross guiding passages, said first distal segment and said second distal spacing disk in sequence; and said structural backbone cross guiding passages are in a left-right crossed arrangement in a horizontal direction or in an upper-lower crossed arrangement in a vertical direction, so that one end of said second proximal segment structural backbone at a left part of said proximal segment connects to one end of said second distal segment structural backbone at a right part of said second distal segment, and one end of said second proximal segment structural backbone at a right part of said proximal segment connects to one end of said second distal segment structural backbone at a left part of said second distal segment; or one end of said second proximal segment structural backbone at an upper part of said proximal segment connects to one end of said second distal segment structural backbone at a lower part of said second distal segment, and one end of said second proximal segment structural backbone at a lower part of said proximal segment connects to one end of said second distal segment structural backbone at an upper part of said second distal segment.

15. The flexible surgical instrument with structural backbones in a crossed arrangement according to claim 14, wherein said flexible surgical instrument further includes a driving handle comprising a driving handle base, a gimble and a linear sliding module; said driving handle base extends through said proximal structural body and connects to one of said two passage fixing plates via said gimble; said driving handle base is connected to said proximal fixing disk via said linear sliding module.

* * * * *